United States Patent [19]
Soffer et al.

[11] 4,123,431
[45] Oct. 31, 1978

[54] NON-OXO-CARBONYL CONTAINING BENZOYL ECGONINE AND COCAINE COMPOUNDS AND DERIVATIVES THEREOF

[75] Inventors: Michael J. Soffer, Los Angeles; Richard S. Schneider, Saratoga, both of Calif.

[73] Assignee: Syva Company, Palo Alto, Calif.

[21] Appl. No.: 794,442

[22] Filed: May 6, 1977

Related U.S. Application Data

[62] Division of Ser. No. 364,842, May 29, 1973, Pat. No. 4,045,420.

[51] Int. Cl.$^2$ .................. C07D 451/12; C07D 451/06
[52] U.S. Cl. ................................ 260/292; 260/293.54
[58] Field of Search ............................ 260/293.54, 292

[56] References Cited

U.S. PATENT DOCUMENTS

| 3,498,989 | 3/1970 | Sallay | 260/292 |
|---|---|---|---|
| 3,912,742 | 10/1975 | Stephen | 260/293.54 |
| 3,917,582 | 11/1975 | Soffer et al. | 260/293.54 |

FOREIGN PATENT DOCUMENTS

1,010,070   6/1957   Fed. Rep. of Germany ........... 260/292

OTHER PUBLICATIONS

Fodor, G., Acta Chim. Acad. Sci. Hung., 5, 375–378 (1955) [Chemical Abstracts, 50, 10113f (1956)].

*Primary Examiner*—Henry R. Jiles
*Assistant Examiner*—Richard A. Schwartz
*Attorney, Agent, or Firm*—Townsend and Townsend

[57] ABSTRACT

Non-oxo-carbonyl substituted derivatives of cocaine are provided for conjugation with other compounds to provide reagents for use in a diversity of immunoassay techniques. Specifically, carboxy or imidoyl derivatives are provided which may be conjugated with antigens for use in the preparation of antibodies to cocaine or conjugated with detector molecules for use in the qualitative or quantitative determination of the presence of cocaine.

16 Claims, No Drawings

NON-OXO-CARBONYL CONTAINING BENZOYL ECGONINE AND COCAINE COMPOUNDS AND DERIVATIVES THEREOF

Cross Reference to Related Applications

This is a divisional of application Ser. No. 364,842 filed May 29, 1973, now U.S. Pat. No. 4,045,420.

BACKGROUND OF THE INVENTION

1. Field of the Invention

A wide variety of ways have been developed for determining minute quantities of various organic compounds. A number of methods which can be used for the determination of organic compounds depend on the availability of a receptor which recognizes a particular compound or class of compounds. The most common type of receptor is the antibody which is also to strongly bind to a particular spatial conformation and polar or non-polar distribution.

In order to prepare the antibodies for compounds which are not antigenic, the non-antigenic compound is normally bonded to an antigenic material, particularly a protein. With most compounds, it is found necessary to modify the compound of interest to bond to the antigen.

In addition, in some of the immunoassays, it is necessary to bond the compound to a detector molecule. The link that is chosen for bonding to the antigen and to the detector molecule must allow not only for satisfactory bonding to the various molecules, but also must provide an antibody which recognizes the compound when it is bound to the detector molecule.

In addition, the linking group must not significantly change the polar characteristics of the compound to be assayed nor detrimentally affect the molecules to which the compound is bonded. Depending on the particular material to which the compound is to be bonded, the linking group should permit a sufficient number of the desired compound to be bonded to the antigen or detector molecule. Additional considerations include synthetic simplicity, chemical stability, the effect of the bonding functionality on the material to which it is bonded, and the particular site on the material for example, a protein, to which the compound will be bonded.

2. Description of the Prior Art

An immunoassay technique employing a stable free radical detector, entitled FRAT®, supplied by Syva Corporation, is described in U.S. Pat. No. 3,690,834. Another immunoassay technique using enzymes as a detector and commercially available as EMIT$^{TM}$, supplied by Syva Corporation, is found in copending application, Ser. No. 143,609 filed May 14, 1971, now abandoned. Radioimmunoassay is described in a number of texts for example Kirkham, et al, Radioimmunoassay Methods, Churchill, Livingston, London, 1971. A description of a number of derivatives of cocaine and ecgonine may be found in Pelletier, Chemistry of the Alkaloids, Van Nostrand-Reinholt, New York, 1970. U.S. Pat. No. 3,498,989 also discloses a number of cocaine derivatives.

SUMMARY OF THE INVENTION

Cocaine derivatives are provided having non-oxo-carbonyl functionalities for bonding to amino groups, particularly amino groups of proteins or amino groups present in stable free radicals. The compounds of this invention are bonded to proteins, either to provide an antigenic material for production of antibodies to ecgonine or cocaine, or bonding to enzymes to provide a reagent for use in immunoassays. Alternatively, the compounds of this invention may be bonded to amino substituted stable free radicals to provide a detector molecule for use in FRAT®.

DESCRIPTION OF THE SPECIFIC EMBODIMENTS

The compounds of this invention are derivatives of nor-tropane which are able to be used for preparing antibodies to cocaine, as well as be bonded to detector molecules for use in immunoassays.

Ecgonine is 2-carboxy-3-hydroxytropane. Cocaine is the methyl ester of 2-carboxy-3-hydroxytropane benzoate. The derivatives of this invention will be either at the 3 position, or the 8 position of the nor-tropane ring.

For the most part, the compounds of this invention will be of from 10 to 25 carbon atoms and from 6 to 7 heteroatoms which will be oxygen and nitrogen. More usually, the compounds of this invention will be of from 16 to 22 carbon atoms and from 6 to 7 heteroatoms, which are oxygen and nitrogen. There will usually be from 0 to 2 sites of ethylenic unsaturation, more usually from 0 to 1 site of ethylenic unsaturation. The heterofunctionalities will be limited to non-oxo-carbonyl and nitrogen analogs thereof, and amino. The non-oxo-carbonyl functionalities include esters, carboxylic acids, carboxylic acid anhydrides, and imidates.

For the most part, the compounds of this invention will have the following formula:

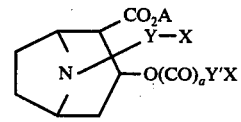

wherein
A is hydrogen or methyl;
one of Y and Y' is hydrocarbylene; aliphatic, alicyclic, aromatic or combinations thereof, of from 1 to 10 carbon atoms, more usually of from 1 to 8 carbon atoms, wherein Y—X is methyl when Y' is hydrocarbylene and Y'X is phenyl or hydrogen when Y is hydrocarbylene;
X, when bonded to a hydrocarbylene, is a non-oxo-carbonyl functionality, including nitrogen analogs thereof, including carboxylic acid, carboxylic acid esters of from 2 to 8 carbon atoms, imidates of from 1 to 8 carbon atoms, more usually from 1 to 4 carbon atoms, and mixed anhydrides, particularly carbonic acid anhydride, of from 3 to 10 carbon atoms, more usually 3 to 8 carbon atoms; and $a$ is zero when Y'X is hydrogen and one when Y'X is other than hydrogen.

The hydrocarbylene may be straight chain or branched, usually having not more than one branch per 2 carbon atoms, the branch usually being methyl. For the most part, the hydrocarbylene will either be aliphatic or aromatic, generally being monocyclic. If alicyclic, the ring will normally be of from 5 to 6 carbon atoms.

Illustrative hydrocarbylene groups include methylene, ethylene, butylene, hexylene, phenylene, tolylene, benzylene, cyclohexylene, propenylene, hexenylene, 1,4-pentenylene, etc.

For those compounds which have the non-oxo-carbonyl derivative at the 8 position, they will, for the most part, come within the following formula:

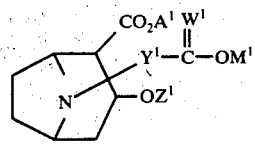

wherein
$A^1$ is hydrogen or methyl, usually methyl;
$Z^1$ is hydrogen or benzoyl, usually benzoyl;
$Y^1$ is hydrocarbylene of from 1 to 10 carbon atoms, more usually of from 1 to 8 carbon atoms, and usually of from 0 to 1 site of ethylenic unsaturation, and may be aliphatic, alicyclic of aromatic or combinations thereof, usually aliphatic of from 1 to 6 carbon atoms;
$W^1$ is oxygen or —NH—; and
$M^1$ is hydrogen, hydrocarbon of from 1 to 8 carbon atoms, more usually of from 1 to 6 carbon atoms, usually being other than hydrogen when $A^1$ is hydrogen; and preferably alkyl of from 1 to 4 carbon atoms, or alkoxycarbonyl when $W^1$ is oxygen, so as to form a mixed anhydride with carbonic acid. The alkyl group will normally be of from 1 to 6 carbon atoms, more usually of from 2 to 6 carbon atoms. When $M^1$ is alkoxycarbonyl, $A^1$ will be methyl.

Illustrative compounds include 8-carboxymethyl-nor-ecgonine, 8-(para-carboxybenzyl)nor-ecgonine benzoate methyl ester; 8-(4'-carboxybut-2-enyl)nor-ecgonine benzoate methyl ester; 8-(3'-ethoxyiminopropyl)nor-ecgonine benzoate methyl ester; and 8-(para-butoxyiminobenzyl)nor-ecgonine benzoate methyl ester.

Where the non-oxo-carbonyl is at the 3 position, the compounds will, for the most part, having the following formula:

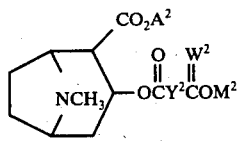

wherein
$A^2$ is hydrogen or methyl, usually methyl;
$Y^2$ is hydrocarbylene of from 6 to 10 carbon atoms having a benzene ring, usually of from 6 to 8 carbon atoms, and usually arylene or aralkylene, e.g. phenylene or phenalkylene;
$W^2$ is oxygen or —NH—; and
$M^2$ is hydrogen, hydrocarbon of from 1 to 8 carbon atoms, usually of from 1 to 6 carbon atoms, particularly alkyl of from 1 to 4 carbon atoms or alkoxycarbonyl, wherein the alkyl group is of from 1 to 6 carbon atoms. When $M^2$ is alkoxycarbonyl or hydrogen, $A^2$ will be methyl. When $W^2$ is —NH—, $M^2$ is hydrocarbon.

Illustrative compounds include para-carboxybenzoyloxyecgonine methyl ester; meta-methoxyiminobenzoyloxyecgonine methyl ester; para-(2-[1'-butoxyimino]ethyl)benzoyloxyecgonine methyl ester; and para-(1-carboxy-2-propyl)benzoyloxyecgonine methyl ester.

For the most part, substituents on the aromatic rings will be either meta or para, more usually para. That is, substituents will be separated by at least 3 annular members, there generally being not more than 3 substituents on a ring, more usually not more than 2 substituents on a ring.

Of particular interest for the use of the subject compounds are the non-oxo-carbonyl substituted cocaine or ecgonine or nitrogen analogs thereof, particularly substituted benzoyl ecgonine, bonded to an amino group, which is part of a polypeptide structure. One group of polypeptides is antigenic, so that by bonding the non-oxo-carbonyl modified cocaine, ecgonine, or benzoyl ecgonine to the polypeptide, antibodies can be formed to cocaine and its metabolites. A narrower class of polypeptides which also can be used as antigens but will not normally be used as such, are enzymes which are employed as the detector in an immunoassay system.

Polypeptides usually encompass from about 2 to 100 amino acid units (usually less than about 12,000 molecular weight). Larger polypeptides are arbitrarily called proteins. Proteins are usually composed of from 1 to 20 polypeptide chains, called subunits, which are associated by covalent or non-covalent bonds. Subunits are normally of from 100 to 300 amino acid groups (approximately 10,000 to 35,000 molecular weight). For the purposes of this invention, polypeptide is intended to include individual polypeptide units, or polypeptides which are subunits of proteins, whether composed solely of polypeptide units or polypeptide units in combination with other functional groups, such as porphyrins, as in hemoglobin or cytochrome oxidase.

The first group of protein materials or polypeptides which will be considered are the antigenic polypeptides. These may be joined to the non-oxo-carbonyl group or nitrogen analog thereof substituted on the cocaine, ecgonine or benzoyl ecgonine, through an amino group. The amide or amidine product can be used for the formation of antibodies to cocaine or its metabolites. The polypeptide materials which may be used will vary widely, normally being of from about 1,000 to 10 million molecular weight, more usually from 12,000 to 500,000 molecular weight.

With most conventional polypeptides, there will not be more than about one cocaine or derivative group per 1,500 molecular weight of polypeptide, usually not more than one group per 2,000 molecular weight. There will be at least one group per 500,000 molecular weight, usually at least one per 50,000 molecular weight. With intermediate molecular weight antigens (50,000 to 1 million) the number of cocaine or derivative groups will generally be from about 2 to 250, usually from 10 to 100.

With low molecular weight antigens, 1,000 to 5,000, the number of cocaine or derivative groups will be in the range of 1 to 10, usually in the range of 2 to 5, so that there may be as many as one cocaine or derivative per 500 molecular weight of polypeptide.

Usually, the number of groups bonded to the polypeptide will be related to the available amino groups, e.g. the number of lysines present. While the cocaine or derivative may be bonded through the non-oxo-carbonyl group to hydroxyl or mercaptan groups, which are present in the polypeptide, for the most part the bonding will be to amino and therefore, the compounds are described as amides or amidines. However, esters and thioesters and their nitrogen analogs may also be present.

Amino acids present in proteins which have free amino groups for bonding to the non-oxo-carbonyl modified cocaine or derivative thereof include lysine, arginine, histidine, etc. The hydroxylated and mercaptan substituted amino acids include serine, cysteine and threonine.

Various protein types may be employed as the antigenic material. These types include albumin, serum proteins, e.g. globulins, ocular lens proteins, lipoproteins, etc. Illustrative proteins include bovine serum albumin, key-hole limpet hemocyanin, egg ovalbumin, bovine γ-globulin, etc. Small natural polypeptides which are immunogenic, such as gramicidin may also be employed. Various synthetic polypeptides may also be employed, such as polymers of lysine, glutamic acid, phenylalanine, tryosine, etc., either by themselves or in combination. Of particular interest is polylysine or a combination of lysine and glutamic acid. Any synthetic polypeptide must contain a sufficient number of active groups, as for example, amino groups provided by lysine.

The second group of polypeptides or protein molecules are the enzymes to which the non-oxo-carbonyl derivative may be conjugated. As indicated, the cocaine derivative modified enzyme is useful for immunoassays. The immunoassay technique will follow in more detail.

Various enzymes may be used such as oxidoreductases, hydrolases, lyases, and the like. These enzymes include esterases, amidases, phosphorylases, carbohydrases, oxidases, reductases and the like. Of particular interest are such enzymes as lysozyme, amylase, dehydrogenases, particularly malate dehydrogenase, lactate dehydrogenase, mannitol-1-phosphate dehydrogenase, and glucose 6-phosphate dehydrogenase, β-glucuronidase, cellulase and, phospho-lipase, particularly phospholipase C. The enzymes will usually have molecular weights in the range of about $1 \times 10^4$ to $6 \times 10^5$, more usually in the range of about $1.2 \times 10^4$ to $3 \times 10^5$.

There will usually be at least one cocaine or derivative group per enzyme molecule, and usually not more than one group per 1,500 molecular weight, usually not more than one group per 2,000 molecular weight. Usually there will be at least one cocaine or derivative group per 50,000 molecular weight, and more usually at least one group per 30,000 molecular weight. The modified enzyme will retain on the average at least 10%, more usually at least 30% of the original activity of the unmodified enzyme.

Where the cocaine or derivative is bonded to a polypeptide, there need by only one cocaine or derivative group, but usually there will be at least two groups. With the enzymes, the number of cocaine or derivative groups will generally be of from 1 to 30, more usually 2 to 25. Usually there will be at least 2, more usually at least 3, groups per enzyme, when the enzyme is randomly substituted with the cocaine or derivative groups and preferably not more than 16.

The substituted polypeptides will, for the most part, have the following formulae:

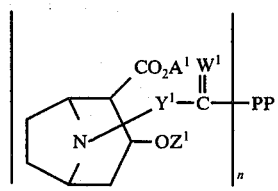

(a)

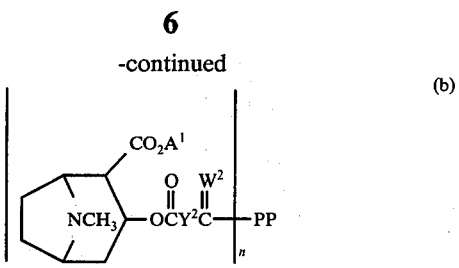

(b)

wherein
$A^1$ and $A^2$, $Y^1$ and $Y^2$, $W^1$ and $W^2$ and $Z^1$ have all been defined previously, and $n$ is the number of groups bonded to PP, the polypeptide, particularly enzymes, and for enzymes is usually in the range of 1 to 30, more usually in the range of 1 to 25, and most usually in the range of 2 to 16.

Instead of an enzyme, a stable free radical may be employed as the functionality for detection in the immunoassay. These stable free radicals are cyclic nitroxides, having the nitrogen of the nitroxide as an annular member and from 0 to 1 other heteroatoms, i.e. oxygen and nitrogen, as annular members.

The molecules bonded to the derivatives of cocaine or ecgonine will normally be of from 8 to 16 carbon atoms, usually of from 8 to 12 carbon atoms. The functionality for linking to the cocaine or ecgonine derivative may be bonded directly to an annular carbon atom or bonded to an annular carbon atom through an aliphatic chain of from 1 to 4 carbon atoms, usually of from 1 to 2 carbon atoms. The molecules may have from 0 to 2 sites of ethylenic unsaturation, more usually from 0 to 1 site of ethylenic unsaturation.

For the most part, the stable nitroxide functionalities which are employed will have the following formula:

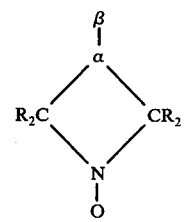

wherein
α is a divalent aliphatic radical, having from 0 to 1 site of aliphatic unsaturation, usually aliphatically saturated of from 1 to 6 carbon atoms, usually from 2 to 3 carbon atoms being annular atoms;
R is lower alkyl (1 to 6, usually 1 to 3 carbon atoms) preferably methyl; and
β is one of the following formulae:

(a)

(b)

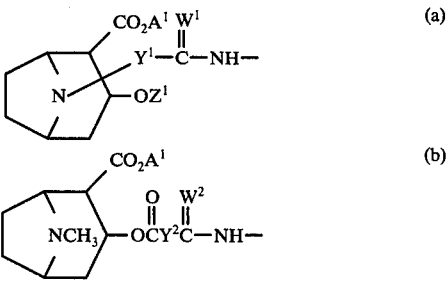

wherein all of the symbols have been defined previously.

For the most part, the cyclic nitroxides are pyrrolidine or piperidine derivatives.

Illustrative spin labeled compounds include N-(1'-oxy-2',2',5',5'-teramethylpyrrolidinyl-3') 2-(N''-nor-cocainyl)-acetamidine; N-(1'-oxyl-2',2',5',5'-tetraethyl-pyrrolidinyl-3') 4'-(N''-nor-cocainyl)butyramide; N-(1'-oxyl-2',2',6',6'-piperidinyl-4') 3-(N''-nor-cocainyl)propionamide and N-(1'-oxyl-2',2',6',6'-piperidinyl-4') para-(2-carboxy-3-tropanyloxycarbonyl)phenylacetamidine methyl ester.

The compounds of this invention may be prepared in a variety of ways. Conveniently, nor-ecgonine or non-cocaine can be used to displace chlorine or bromine on a haloaliphatic carboxylic acid. The acid may then be activated employing carbodiimide, or alternatively, and preferably, the mixed anhydride can be prepared employing a chloroformate ester and a tertiary amine. Where nitrile groups are present in place of the carboxylic acid, the imidate can be prepared by conventional techniques.

The conditions for conjugation of the compound with polypeptides are normally quite mild. Usually, with the mixed anhydride a constant basic pH in the range of 8 to 10 is maintained by the continued monitoring of the system. The imidate is preferred, in that it is a milder reagent than the mixed anhydride.

Antibodies

The preparation of antibodies specific for haptenic materials is a well established practice. A thorough description of the procedure may be found in Williams et al, Methods in Immunology and Immunochemistry, Academic Press, New York and London, 1967, page 197 to 385, particularly that portion beginning at 197 and ending at 254.

For preparation of antibodies to haptens, a hapten is conjugated to an antigenic material such as a polypeptide or protein, although polysaccharides, particularly containing amino sugars, can also be used.

The particular manner in which the hapten is bonded to the antigenic material will depend on the functionalities which are available on the haptenic material and the antigenic material, the number of haptenic groups to be conjugated to the antigenic material, and the like. Groups which find use include carboxy groups, which may be activated by employing the mixed carbonic acid anhydride or carbodiimide, imidates, diazo groups, α-haloketones, and the like. Numerous procedures for the conjugation of a wide variety of haptens have been developed and published.

The antigenic conjugate may be injected in the fluid state; absorbed to insoluble particles, such as alumina; or incorporated in matrix materials such as agar, calcium alginate, or Freund's adjuvants ("complete" or "incomplete," depending on whether mycobacteria are incorporated). The adsorption to various insoluble colloidal carriers is described in the aforementioned text, the carriers being illustrated by alumina, aluminum phosphate, blood charcoal, and the like. Other materials include polyacrylamide gel, bentonite, and protein. As adjuvants, methylated bovine serum albumin and Freund's adjuvant find use. Complete Freund's adjuvant is a water-in-oil emulsion, using emulsion stabilizers such as lanolin, lanolin derivatives, e.g. Aquaphor, mannide mono-oleate and Arlacel A, available from Duke Laboratories, South Newark, Connecticut. The complete adjuvant is distinguished from the incomplete adjuvant by having mycobacteria e.g. *M.butyricum* or *M.tuberculosis*. The adjuvants are commercially available from Difco Laboratories, Detroit, Mich.

Immunization can be carried out in a variety of ways with a number of different animals. For the most part, for commercial production of antibodies, relatively large animals are employed, such as equinine, bovine, porcine, canine, ovine, caprine, rodentia, rabbits, and hares. Of particular interest are horses, goats, sheep, and cows, that is, the larger domestic animals, as well as rabbits.

The antigenic material may be injected interperitoneally, intramuscularly, subcutaneously, and the like. When employing Freund's adjuvants, usually in combination with saline, the amount of antigen employed will vary depending on the particular antigenic material and the number and period of prior injections. Usually, about 0.1 to 5 mg of antigenic material will be employed per one ml of solution. The total amount of antigenic material and solution will depend on the size, nature, and weight of the animal employed. The initial injection will normally be at a number of sites, aliquots of the composition being employed.

The first injections of antigen serve to load the animal, and a period of time is allowed to pass before booster injections are introduced, normally two to five weeks. Bleeding may occur after each injection, so as to follow the formation of the desired antibody. Depending on the animal, bleedings can be carried out via heart puncture, the carotid artery or external jugular vein. The bleeding will usually be carried out about one week after an injection. The blood may then be combined with a small amount of sodium citrate, the mixture agitated and then the erythrocytes settled by standing or centrifugation. The plasma is drawn off and combined with calcium chloride, with clotting resulting. If necessary, thrombin may be added to enhance clotting. After breaking up the clot, the clot is compressed and serum is withdrawn and filtered. Various other procedures are known and can be employed.

The serum can be treated in various ways, depending on its subsequent use. The serum may be fractionated by employing ethanol, neutral salts such as ammonium sulfate or sodium sulfate, or the like. Alternatively, the serum may be chromatographed on various modified cellulose columns, e.g. diethylaminoethylcellulose or carboxymethylcellulose or, various physical means may be employed to concentrate the desired antibodies. Usually, the product will be dialyzed after dissolution in a buffer, filtered and then isolated.

Numerous preservatives can be employed to stabilize the antibodies and the antibodies will normally be stored at reduced temperatures.

The antibodies are primarily γ-globulin which are found to have a molecular weight of about 150,000. The antibodies will be specific for a particular spatial structure and polar - non-polar distribution. Varying structures deviating from an ideal structure will give different binding constants.

The following examples are offered by way of illustration and not by way of limitation.

Experimental (All temperatures not indicated are in Centigrade.)

EXAMPLE A.

Preparation of Cocaine and Cocaine Metabolite Antibodies

Employing an antigen prepared in accordance with Example VII, infra, a sheep was injected with 2 cc of a solution with 0.5 cc aliquots of 4 subcutaneous sites and 1 cc intramuscularly in each hind leg. The solution was comprised of 10 mg of the antigen in 1 ml sline, and 3 ml incomplete Freund's adjuvant. Repeated injections were carried out on an approximately monthly basis of a solution containing 10 mg of the antigen, 1 ml saline, and 3 ml incomplete Freund's adjuvant. For the fifth and sixth injections, the injected material had 2 mg of antigen, 1 ml of saline, and 3 ml of incomplete Freund's adjuvant.

The animals were bled about one week after each injection, either to follow the course of antibody formation or to obtain a supply of antibodies. About one week after the last injection, the animal was bled, approximately 500 cc of blood being mixed with 10 ml of 25% sodium citrate. The mixture was then centrifuged at 5,000 rpm for 20 minutes. The plasma was aspirated off and mixed with 10 ml of 25% calcium chloride. In order to enhance clotting, 2 NIH units of thrombin per ml of plasma was added and the mixture allowed to stand overnight at about 35° C.

The resulting clot was chopped up and the mixture centrifuged at 5,000 rpm for about 30-45 minutes at 5° C. The serum was then filtered through glass wool and isolated. To the serum was then added dropwise an equal volume of saturated ammonium sulfate in water with constant stirring at 4° C. After allowing the mixture to stand for one hour at that temperature, the mixture was centrifuged at 10,000 rpm for 30 minutes. The supernatant was decanted, and the precipitate ($\gamma$-globulin) was resuspended in 0.4M, pH8, borate buffer, containing 1 g/l of sodium azide and 0.1 g/l. of Thimerosal. Initially, buffer is added at one half the original serum volume and addition is continued until the precipitate is dissolved. The solution is then dialyzed continuously against 4 liters of the same buffer, after which it is filtered through a 22 millipore filter. The product is then ready for use.

The antibody solution was found to have a binding constant of $5.6 \times 10^7$ with cocaine.

The antibodies prepared in response to the antigens of this invention are selective for the indicated cocaine derivative and the conjugate of N-carboxymethyl nor-cocaine to an antigenic protein.

EXAMPLE I

3-(N'-nor-cocainyl)acetamido)-2,2,5,5-pyrrolidinyl-1-oxyl

A. A solution of 1.33 g (4.6 mmole) of benzoyl ecgonine in 200 ml water was adjusted to pH 9 with a few drops of sodium hydroxide. Potassium permanganate (61 ml of 3% aqueous solution) was added dropwise with good stirring at 25°. After 18 hours at room temperature, the solution was cooled to 5° and 50 ml ethanol was added to destroy excess oxidant. After stirring for 1 hour, the reaction mixture was filtered through Celite and the pH of the filtrate adjusted to 4 with 1N hydrochloric acid. The aqueous solution was evaporated to dryness in vacuo. Care was taken to maintain the temperature at less than 35° to prevent debenzoylation. The residue was triturated twice with hot ethanol and filtered. The ethanol was evaporated and the residue recrystallized from ethanol to give 0.875 g of colorless crystals; m.p. 227°-230°.

Anal. Calcd. for $C_{15}H_{17}NO_4.HCl.C_2H_5OH$: C, 57.05; H, 6.76; N, 3.91; Cl, 9.91 Found: C, 56.78; H, 6.52; N, 3.85; Cl, 9.89.

B. A solution of 1.50 g benzoyl nor-ecgonine hydrochloride in 50 ml methanol was saturated with dry hydrogen chloride. The reaction mixture was then refluxed for one hour before being evaporated to a light yellow oil. The residue was dissolved in chloroform, washed once with dilute base and then evaporated to give 1.106 g of yellow oil. The product was chromatographed on silica gel using chloroform as the initial eluent. After a few minor impurities were eluted nor-cocaine was removed with 10% methanol in chloroform and was recovered as a colorless oil.

C. A solution of 1.43 g (5.2 mmole) nor-cocaine and 0.840 g (6.25 mmole) sodium bromoacetate was refluxed under nitrogen for 3 hours in 10 ml of anhydrous methanol The reaction was judged to be complete at this point by TLC with 10% methanol-chloroform. The solution was evaporated to dryness before 10 ml chloroform and 15 ml water were added. The pH of the aqueous phase was adjusted to 3-4 with 1N hydrochloric acid. The chloroform phase was washed once with water and evaporated to give 0.470 g nor-cocaine. The aqueous phase was washed once with chloroform and evaporated in vacuo at 35°. The N-carboxymethyl nor-cocaine crystallizes as the solution is concentrated. A total of 1.75 g was recovered in this manner and was recrystallized from water: m.p. 173°-178°.

Anal. Calcd. for $C_{18}H_{21}NO_5.HCl$: C, 56.32, H, 5.77; N, 3.65; Cl, 9.25. Found: C, 55.92; H, 5.80; N, 3.49; Cl, 9.06

D. To a solution of 0.041 g (0.2 mmole) dicyclohexylcarbodiimide and 0.028 g (0.2 mmole) of 3-amino-2,2,5,5,-tetramethylpyrrolidinyl-1-oxyl in 2 ml of ethyl acetate and 2 ml dichloromethane was added 0.067 g (0.2 mmole) N-carboxymethyl nor-cocaine. The reaction was stirred at 25° for 24 hours, the urea was filtered, and the filtrate was evaporated to dryness. The residue was purified by preparative TLC (10% methanolchloroform) on silica gel. The product, isolated as a crystalline light yellow solid, has a 3 line ESR spectrum $a_N(H_2O) = 16.5G$.

EXAMPLE II

Conjugate of N-carboxymethyl nor-cocaine with bovine serum albumin (BSA).

To 10 ml dry DMF containig 0.42 g ($1.0 \times 10^{-3}$ mmoles) of the hydrochloride of N-carboxymethyl nor-cocaine was added 0.15 g ($1.1 \times 10^{-3}$ mmoles) isobutyl chloroformate and 0.11 g ($1.1 \times 10^{-3}$ mmoles) triethylamine. The mixture was stirred at $-15°$ under $N_2$ for 1.5 hours. To the reaction mixture was added 0.68 g bovine serum albumin (BSA) at 4° in 100 ml water with 1 g $NaHCO_3$. An additional 70 ml water was added and the mixture stirred overnight. The resulting homogenous solution was dialyzed against water for three days, changing the water 3 times the first day and two times on successive days. The resulting product was lyophilized to dryness, yielding 0.77 g. By U.V. analysis, the degree of conjugation was determined to be 22.4.

EXAMPLE III

5-(N-nor-cocainyl)valeric acid

A. nor-Cocaine (100 mg, 0.346 mmole) benzyl 5-bromovalerate (164 mg, 0.623 mmole), diisopropylethyl amine (130 mg, b.p. 126°/760 mm Hg, 1.04 mmoles) and potassium iodide (200 mg) were refluxed in dry benzene (5 ml) with continuous stirring for 12 hours until the starting nor-cocaine disappeared, as shown by TLC (silica gel, $R_f$ 0.45, 5% methanol — 95% chloroform). The cooled mixture was diluted with ether and the precipitate was separated and was removed by suction filtration. The filtrate was washed with water, dried, condensed and purified by preparative TLC (silica gel) using chloroform containing 5% methanol as solvent. A band with $R_f$ value of 0.8 was collected by cutting and extracted with acetone. Removal of the acetone left an oil, which was dissolved in dichloromethane, washed with water, and dried over anhydrous sodium sulfate. The dichloromethane solution was evaporated to dryness and gave a colorless oil (140 mg) of the product in 92% yield: IR (neat) 1730, 1715, 1600 and 1584 cm$^{-1}$.

Anal. Calcd. for $C_{28}H_{33}NO_6$: C, 70.12; H, 6.94; N, 2.92. Found: C, 70.11; H, 7.08; N, 2.91.

B. The benzyl ester prepared above (70 mg, 0.149 mmoles) in ethyl acetate (4 ml) was hydrogenolyzed over 10% palladium on charcoal (35 mg) at 20° for 30 minutes, at which time 4.0 ml of hydrogen (0.154 mmoles) had been absorbed. After removal of the catalyst, the solvent was evaporated to leave a colorless oil, which was treated with a small amount of a 1:5 solution of ether and petroleum ether. The insoluble heavier oil was evaporated to dryness to afford a colorless oil (50 mg, 81%) of the product, which on purification by preparative TLC (silica gel, 10% methanol — 90% chloroform) gave an analytically pure oil.

Anal. Calcd. for $C_{21}H_{27}NO_6$: C, 64.76; H, 6.99; N, 3.60. Found: C, 64.13; H, 7.56; N, 3.60.

EXAMPLE IV

4-(N-nor-cocainyl)crotonic acid

A. Nor-cocaine (100 mg, 0.358 mmole), benzyl 4-bromocrotonate and diisopropylethylamine (130 mg, 1.07 mmoles) in dry benzene (5 ml) was refluxed with continuous stirring for 2 hours. The mixture was cooled, and the precipitate which separated was removed. The filtrate was diluted with ether (10 ml) and then washed with water and dried over anhydrous sodium sulfate. After removal of solvents, the oil obtained was purified by preparative TLC (silica gel, 1:1 ether/petroleum ether), to give analytically pure benzyl 4-(N-nor-cocainyl)crotonic (130 mg, 81%), showing one spot ($R_f$).45 one TLC, Anal. Calcd. for $C_{27}H_{29}NO_6$: C, 69.95; H, 6.31; H, 3.02. Found: C, 69.76; H, 6.36; N, 2.95.

B. Hydrogenolysis of the above ester (208 mg, 0.605 mmole) was carried out in the presence of 10% palladium on charcoal (30 mg) at 22° in ethyl acetate (5 ml) and ceased after 30 minutes, when 35.6 ml of hydrogen (1.47 mmoles) had been consumed. After being worked up as usual, there was obtained 237 mg of an oil (54% yield) with $R_f$ value of 0.70, 17 mg of a solid, m.p. 200°-230°, with $R_f$ value of 0.62, and 27 mg of oil with $R_f$ value of 0.05. The most mobile oil was identical with nor-cocaine in all respects.

The above product, according to prior procedure, could be spin labeled with 3-amino-2,2,5,5-tetramethylpyrrolidinyl-1-oxyl to provide the product 3-[4'-(N-nor-cocainyl)crotonamido]-2,2,5,5-tetramethylpyrrolidinyl-1-oxyl.

EXAMPLE V

(N-nor-Cocainyl) valeric acid conjugate to Lysozyme

A. (N-nor-Cocainyl)valeric acid (12.0 mg, 30.9 μmole) in 0.5 ml of DMF containing two drops of triethylamine was treated with an equimolar amount of isobutyl chloroformate and the reaction mixture stirred for two hours.

B. Lysozyme (37.0 mg, 15.5 μmole) was dissolved in 4 ml of water, the solution cooled to 0° and the pH adjusted to 9.5. The mixed anhydride prepared above was added dropwise. The pH was maintained with dilute base near about 9.5 during the 45 minute reaction time. At the end of the addition, the pH was adjusted to 7.4, a small quantity of precipitate which formed was removed by centrifugation and thus the supernatant enzyme activity was found to be inhibited up to 86% on addition of anti-cocaine antisera. The insoluble portion was dissolved in 8M urea, and dialyzed against water. Only 2% of the total enzyme was found in this portion. Inhibition of enzymatic activity with goat anti-cocaine could be accomplished to 94.3%. Up to 60% of the enzymatic activity can be regenerated upon addition of cocaine.

EXAMPLE VI.

Preparation of $O^3$-(para-[α-methoxyimino]toluoyl) ecgonine.

A. To a solution of 2.61g (13 mmoles) methyl ecgoninate in 40ml dry benzene was added 1.12g (6.3 mmoles) p-cyanomethylbenzoyl chloride in 10ml benzene. The reaction was stirred for 24 hours at 25° during which time a colorless precipitate was formed. The mixture was filtered and the filtrate evaporated to a yellow oil. This oil was chromatographed on silica gel with chloroform. Crystallization from methanol - water gave a solid. m.p. 75°-80°.

B. A suspension of 0.33g (1.0 mmole) of para-cyanomethylcocaine in 5ml dioxane and 5ml water is allowed to stir at reflux for 24 hours. During this time the solution becomes completely homogeneous and the reaction is judged complete by the absence of the starting material by TLC. The solvents are evaporated in vacuo to give a white crystalline solid.

C. To a solution of 0.36 g (1.0 mmole) $O^3$-(paracyanomethylbenzoyl) ecgonine in 10 ml absolute methanol is added 0.006 g (0.1 mmole) sodium methoxide. The reaction mixture is allowed to stir at 25° for 4 hours before evaporating to dryness. The product is isolated as a light yellow foam which can be characterized by its infrared spectra, but due to its high sensitivity, should be used immediately for subsequent reactions.

EXAMPLE VII

$O^3$-(para-methoxyiminobenzoyl) ecgnine

A. To a solution of 0.56 g (3.0 mmole) methyl ecgonate in 10 ml dry benzene and 0.33 g (3.3 mmole) dry triethyl amine was added 0.514 g. (3.1 mmole) para-cyanobenzoyl chloride. The reaction was allowed to stir for 24 hours at 25° during which time a copious precipitate of salt was formed. The reaction mixture was then diluted with water and benzene and the aqueous phase made alkaline to pH 9.0 with dilute base. The aqueous phase was washed several times with benzene and the organic phases were combined and dried over sodium sulfate. The benzene was evaporated giving a light yellow crystalline solid which was recrystallized from benzene to give 0.90 g of the desired product.

B. A suspension of 0.1 g para-cyanococaine in 5 ml dioxane and 5 ml water is refluxed for 24 hours or until no trace of the starting material is visible by the TLC. The solvents are evaporated in vacuo to give the product.

C. To a solution of 0.35 g (1.0 mmole) $O^3$-(paracyanobenzoyl) ecgonine in 10 ml absolute methanol is added 0.0069g (0.1 mmole) sodium methoxide. The reaction mixture is allowed to stir at room temperature for two days before the solvent is evaporated to dryness. Due to the high reactivity of this imino ester, the compound should be used for subsequent reactions immediately upon isolation.

EXAMPLE VIII

Preparation of N-methoxyiminomethyl nor-cocaine

A. To a solution of 0.29 g (1.0 mmole) nor-cocaine and 0.38 g (5.0 mmole) of chloroacetonitrile in 10 ml dry acetone was added 1.5 g potassium carbonate and the mixture allowed to reflux for 24 hours. After cooling, the insoluble material was filtered and the supernatent was evaporated to dryness. The resulting yellow oil was purified by chromatography on silica gel (9:1 chlorofrom:methanol) to give a nearly colorless crystalline solid. The infrared and nmr spectra are in accord with the proposed structure.

B. To a solution of 0.33 g (1.0 mmole) N-cyanomethyl nor-cocaine in 10 ml absolute methanol at 25° is added 0.006 g (0.1 mmole) sodium methoxide. The reaction is allowed to stir at 25° for 24 hours or until little or no trace of N-cyanomethyl nor-cocaine is observable by thin layer chromatography (silica gel, methanol:chloroform 1:9). The methanol is evaporated to dryness.

As already indicated, the compounds of this invention can be conjugated to various antigenic proteins and introduced into vertebrates, such as goats, sheep, horses and the like, according to conventional procedures for producing antibodies. The antibodies can then be harvested and be treated in various ways. For example, the antibodies which are specific for cocaine or cocaine derivatives or metabolites can be concentrated by passing the antibody composition through a column having the cocaine, cocaine derivative or cocaine metabolite bonded to a support. The antibody can then be released from the support by various means known in the art. The antibodies to cocaine or cocaine metabolites can then be used in a variety of assays.

ASSAY

To demonstrate the utility of the compounds of this invention, the compound of Example I was employed in a free radical assay technique, commercially referred to as FRAT®.

Antibodies were prepared by injection of a conjugate prepared in accordance with Example II, having a degree of conjugation of sixteen cocaine derivatives per molecule of BSA. The antigen was injected into two goats and two sheep, the goats being innoculated initially with 15 mg conjugate and boosted every four weeks with 30 mg conjugate. For the sheep, both initial innoculation and boosting (every four weeks) were performed with 15 mg conjugate. All bleeds were made one week after boosting, with one exception.

The γ-globulin or antibodies were prepared from the serum by ammonium sulphate precipitation and dialysis of the re-dissolved precipitate against 0.4 M borate buffer, pH 8.

The spin labelled compound or free radical reagent employed was that of Example I. It was found that the binding constant of the spin labelled compound diminished with time unless the spin labelled compound was stored at pH 5 in the absence of any buffer (however, carbon dioxide was bubbled through the solution) in distilled water (substantially metal ion free). The ratio of γ-globulin active sites to moles of spin labelled compound was 1:1. The final concentration of γ-globulin and spin labelled compound in the assay mixture is 5.28 $\times$ $10^{-6}$M. Buffer was employed to provide a final buffer concentration of 0.18M. In carrying out the assay, 20 μl of sample were combined with 10 μl of combined γ-globulin and spin labelled compound.

In carrying out the test, 50 μl of urine is mixed with 5 μl of 0.2M sodium dichromate. Twenty μl of this sample is added to 10 μl of the γ-globulin spin label solution. The sample is then taken up in an ESR tube which is introduced into the electron spin resonance spectrometer cavity and the ESR signal observed. One or more points of the electron spin resonance spectrometer may be employed in establishing the standards for the cocaine or cocaine metabolite concentration in the sample. The same points would then be used with an unknown. The concentration of cocaine or metabolite would be determined from a graph of concentration resin height detained by graphing standard solutions.

Seventeen urine samples were taken from people who had previously snuffed cocaine. These samples were frozen in small aliquots and assayed about a month later. Eight of the eleven samples taken, 12 or 24 hours after snuffing, read positive.

A number of normal urines were spiked with a variety of drugs to determine any cross-reactivity. At the signal for 1.5 μg cocaine per ml, the normal background cut off point, no interference was detected with 1,000 μg/ml, ecgonine methyl ester, 1,000 μg/ml ecgonine, 1,000 μg/ml benzoyl ecgonine, 1,000 μg/ml scopolamine, 1,000 μg/ml atropine, 1,000 μg/ml homoatropine, 230 μg/ml pentobarbital, 230 μg/ml secobarbital, 230 μg/ml phenobarbital, 100 μg/ml amphetamine, 250 μg/ml ephedrine and 250 μg/ml phenylpropanolamine. The only drug tested which showed any interference above the normal urine background cut off at 1.5 μg/ml cocaine was demerol, which gave 1.6 μg/ml equivalents of cocaine at a concentration of 500 μg/ml demerol. There is substantial similarity between the demerol structure and the cocaine structure.

It is evident from the above results, that the compounds of this invention are useful in preparing antibodies which are highly selective for cocaine. The compounds can also be used in the formation of a number of reagents which can be used in immunoassays, competing with cocaine for antibody sites in an effective manner, so that accurate, quantitative determinations at extremely low concentrations of cocaine can be carried out.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A compound of the formula:

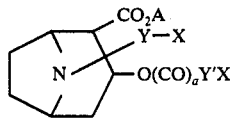

wherein
- A is hydrogen or methyl;
- one of Y and Y' is hydrocarbylene of from 1 to 10 carbon atoms, wherein Y–X is methyl when Y' is hydrocarbylene and Y'X is phenyl or hydrogen when Y is hydrocarbylene;
- X, when bonded to hydrocarbylene, is a non-oxo-carbonyl functionality selected from the group consisting of carboxylic acid, mixed anhydride, and imidate; and
- a is zero when Y'X is hydrogen and one when Y'X is other than hydrogen.

2. A compound according to claim 1, wherein X is a carboxylic acid group.

3. A compound according to claim 1, wherein X is a mixed anhydride.

4. A compound according to claim 1, wherein X is an imidate.

5. A compound of the formula:

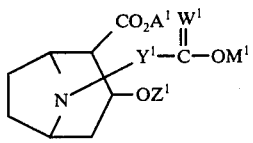

wherein
- $A^1$ is hydrogen or methyl;
- $Z^1$ is hydrogen or benzoyl;
- $W^1$ is oxygen or NH;
- $Y^1$ is hydrocarbylene of from 1 to 10 carbon atoms; and
- $M^1$ is hydrogen, hydrocarbon of from 1 to 8 carbon atoms, or alkoxycarbonyl wherein said alkoxy group is of from 1 to 6 carbon atoms, with the proviso that $M^1$ is other than hydrogen when $A^1$ is hydrogen, $A^1$ is methyl when $M^1$ is alkoxycarbonyl, and $M^1$ is hydrocarbon when $W^1$ is NH.

6. A compound according to claim 5, wherein $Y^1$ is aliphatic of from 1 to 6 carbon atoms, $W^1$ is NH and $M^1$ is hydrocarbon of from 1 to 6 carbon atoms.

7. A compound according to claim 5, wherein $Y^1$ is aliphatic of from 1 to 6 carbon atoms, $W^1$ is oxygen and $M^1$ is alkoxycarbonyl.

8. A compound according to claim 5, wherein $Z^1$ is benzoyl, $A^1$ is methyl and $Y^1$ is aliphatic of from 1 to 6 carbon atoms, having from 0 to 1 site of ethylenic unsaturation.

9. A compound of the formula:

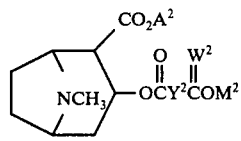

wherein
- $A^2$ is hydrogen or methyl;
- $Y^2$ is hydrocarbylene of from 6 to 10 carbon atoms having a benzene ring in the chain between the two non-oxocarbonyl groups;
- $W^2$ is oxygen or NH; and
- $M^2$ is hydrogen, hydrocarbon of from 1 to 8 carbon atoms, or alkoxycarbonyl, wherein the alkoxy group is from 1 to 6 carbon atoms; with the proviso that when $M^2$ is hydrogen or alkoxycarbonyl, $A^2$ is methyl and when $W^2$ is NH, $M^2$ is hydrocarbon.

10. A compound according to claim 9, wherein $Y^2$ is phenylene and $W^2$ is NH.

11. A compound according to claim 9, wherein $W^2$ is oxygen and $M^2$ is alkoxycarbonyl.

12. A compound according to claim 9, wherein $Y^2$ is phenylene, $W^2$ is NH and $A^2$ is methyl.

13. N-nor-cocainyl acetic acid.

14. 5-(N-nor-cocainyl)valeric acid.

15. $O^3$-(para-[α-methoxyimino]toluoyl)ecgonine.

16. N-(2-methoxyiminoethyl)nor-cocaine.

* * * * *